United States Patent
Tyagi et al.

(10) Patent No.: US 8,304,578 B2
(45) Date of Patent: Nov. 6, 2012

(54) PROCESS FOR PRODUCING 1-[2-(DIMETHYLAMINO)-1-(4-PHENOL)-ETHYL]CYCLOHEXANOL

(75) Inventors: Om Dutt Tyagi, Jinnaram Mandal (IN); Saswata Lahiri, Jinnaram Mandal (IN); Purandhar Koilkonda, Jinnaram Mandal (IN); Jagan Mohana Chary Tummanapally, Jinnaram Mandal (IN); Mohan Vamsi Krishna Vadlamudi, Jinnaram Mandal (IN); Venkata Bala Kishore Sarma Inupakutika, Jinnaram Mandal (IN); Surya Nageswara Rao Achanta, Jinnaram Mandal (IN)

(73) Assignee: Matrix Laboratories Limited, Andhra Pradesh (IN)

( * ) Notice: Subject to any disclaimer, the term of this patent is extended or adjusted under 35 U.S.C. 154(b) by 230 days.

(21) Appl. No.: 12/810,791

(22) PCT Filed: Dec. 26, 2008

(86) PCT No.: PCT/IN2008/000867
§ 371 (c)(1),
(2), (4) Date: Jun. 25, 2010

(87) PCT Pub. No.: WO2009/084039
PCT Pub. Date: Jul. 9, 2009

(65) Prior Publication Data
US 2010/0286447 A1    Nov. 11, 2010

(30) Foreign Application Priority Data
Dec. 26, 2007   (IN) ............... 3108/CHE/2007

(51) Int. Cl.
*C07C 213/02* (2006.01)
(52) U.S. Cl. ...................................... 564/336
(58) Field of Classification Search ............... None
See application file for complete search history.

(56) References Cited

U.S. PATENT DOCUMENTS
4,535,186 A    8/1985    Husbands et al.

FOREIGN PATENT DOCUMENTS
IN          194085        *  1/2011
WO       00/32555           6/2000
WO    2007/094008 A2        8/2007

OTHER PUBLICATIONS

Database CAPLUS on STN, Acc. No. 2010:797935, Sadanand, IN 194085 A1 (Sep. 25, 2004) (abstract).*
INCHE 2006/00824 A (Inogent Labe Private Ltd) Dec. 21, 2007 (abstract, reactions). CASREACT[online] Copyright 2009 ACS on STN [retrieved on Oct. 22, 2009]. Retrieved from: STN International, Karlsruhe. Accession No. 149;425617 CASREACT. Abstract; reaction RX(1) of 1 [Indian patent application 824/CHE/2006].

* cited by examiner

*Primary Examiner* — Brian J Davis
(74) *Attorney, Agent, or Firm* — Workman Nydegger

(57) ABSTRACT

The present invention relates to an improved, process for large scale production of 1-[2-(dimethylamino)-1-(4-phenol) ethyl]cyclohexanol (O-desmethylvenlafaxine) or its pharmaceutically acceptable salts with increased yield and minimal impurities.

21 Claims, No Drawings

PROCESS FOR PRODUCING 1-[2-(DIMETHYLAMINO)-1-(4-PHENOL)-ETHYL]CYCLOHEXANOL

FIELD OF THE INVENTION

The present invention relates to a process for producing 1-[2-(dimethylamino)-1-(4-phenol)ethyl]cyclohexanol (O-desmethylvenlafaxine) or its pharmaceutically acceptable acid addition salts.

BACKGROUND OF THE INVENTION

O-Desmethylvenlafaxine is predominantly active metabolite of venlafaxine and has been shown to inhibit norepinephrine and serotonin uptake. O-Desmethylvenlafaxine succinate marketed in US as PRISTIQ™ and chemically known as 1[2-(dimethylamino)-1-(4-phenol)ethyl]cyclohexanol has the following structure.

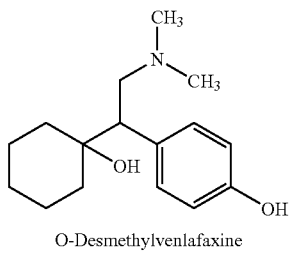

O-Desmethylvenlafaxine

U.S. Pat. No. 4,535,186 filed on Oct. 26, 1983 and granted on Aug. 13, 1985 and assigned to American Home Products corporation claims O-desmethylvenlafaxine as a product and discloses a method of preparation of the same. O-desmethylvenlafaxine is prepared by reacting p-methoxyphenyl acetonitrile with cyclohexanone in the presence of n-butyl lithium at −50° C. in tetrahydrofuran followed by workup to give 1-[cyano(p-methoxyphenyl)methyl]-cyclohexanol. Subsequently, it is subjected to reduction reaction in presence of Rhodium under hydrogen pressure to give 1-[2-amino-1-(p-methoxyphenyl)ethyl]cyclohexanol, followed by alkylation reaction in presence of formaldehyde and formic acid to give venlafaxine and further subjected to O-demethylation to give the O-desmethylvenlafaxine.

According to the prior art processes, p-methoxyphenyl acetonitrile is reacted with cyclohexanone in presence of strong base such as butyl lithium at −80° C. to −50° C. to give 1-[cyano(p-methoxyphenyl)methyl]cyclohexanol. The handling of n-butyl lithium during large scale production at plant level is difficult and poses a fire hazard. Further this reaction is carried out at lower temperature around −80° to −50° C. and the use of strong base such as n-butyl lithium during the condensation reaction results in formation of more impurities. The crude mass so obtained requires repeated crystallization steps to get the desired quality of the product.

WO 2007/094008 application discloses a process for the preparation of O-desmethylvenlafaxine, wherein p-methoxyphenyl acetonitrile is reacted with cyclohexanone in presence of sodium hydroxide and phase transfer catalyst selected from polyethyleneglycol-400 or ALIQUATE 336™ (N-methyl-N,N-dioctyloctan-1-ammonium chloride) to give 1-cyano[(4-methoxyphenyl)methyl] cyclohexanol, which is further subjected to reduction reaction in the presence of reducing agent such as borane-dimethylsulphide complex, aluminum chloride-sodium borohydride to give 1-[2-amino-1-(4methoxyphenyl)ethyl]cyclohexanol. Subsequently, 1-[2-amino-1-(4-methoxyphenyl)ethyl]cyclohexanol is subjected to reductive aviation reaction in presence of formic acid and formaldehyde to give venlafaxine.

Existing processes for the preparation of O-Desmethylvenlafaxine involve use of hazardous chemicals and produces impure O-desmethylvenlafaxine with less yield thereby requiring multiple purification steps that add up to the cost of the final product.

Therefore, there exists a need to develop an alternate and improved process for the preparation of O-desmethylvenlafaxine with improved yield. Further the process involves use of non hazardous chemicals and is simple, convenient and cost-effective for large scale production.

SUMMARY OF THE INVENTION

It is a principal aspect of the present invention to provide an economically viable process for producing 1-[2-(dimethylamino)-1-(4-phenol)ethyl]cyclohexanol (O-desmethylvenlafaxine) or its pharmaceutically acceptable salts in large scale with improved yield and purity.

In accordance with a preferred embodiment of the present invention, there is provided an improved process for producing O-desmethylvenlafaxine or its pharmaceutically acceptable salt thereof, wherein the process comprising reducing 1-[cyano(p-substituted benzyloxyphenyl)methyl]cyclohexanol of formula (II) with a reducing agent sodiumborohydride-iodine or sodiumborohydride-trifluoroacetic acid in presence of a solvent to obtain 1-[2-amino-1-(substituted benzyloxyphenyl)ethyl]cyclohexanol of formula (III), alkylating the resultant to obtain compound of formula (IV) and deprotecting the compound of formula (IV) to obtain O-desmethylvenlafaxine.

In accordance with one other preferred embodiment of the present invention, there is provided a process, wherein the 1-[cyano(substituted benzyloxyphenyl)methyl]cyclohexanol of formula (II) is prepared by reacting substituted benzyloxyphenyl acetonitrile of formula (I) with cyclohexanone in presence of a base and optionally in presence of phase transfer catalyst (PTC) in a solvent.

In accordance with another embodiment of the present invention, there is provided a process, wherein optionally the compound of formula (III) is treated with acid in a solvent to obtain acid addition salts of formula (IIIa) with improved quality.

In accordance with still another embodiment of the present invention, there is provided a process, wherein the O-desmethylvenlafaxine is treated with an acid in a solvent to obtain pharmaceutically acceptable acid addition salt of O-desmethylvenlafaxine.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The present invention relates to an improved, process for large scale production of O-desmethylvenlafaxine or its pharmaceutically acceptable salts with increased yield and minimal impurities.

A process for producing O-desmethylvenlafaxine or its pharmaceutically acceptable salt thereof,

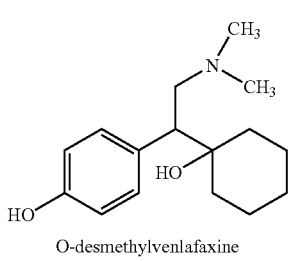

O-desmethylvenlafaxine wherein the process comprising:
a) reducing 1-[cyano(substituted benzyloxyphenyl)methyl] cyclohexanol of formula (II) with reducing agent sodiumborohydride-iodine or sodiumborohydride-trifluoroacetic acid in presence of a solvent to obtain 1-[2-amino-1-(substituted benzyloxyphenyl)ethyl]cyclohexanol of formula (III);

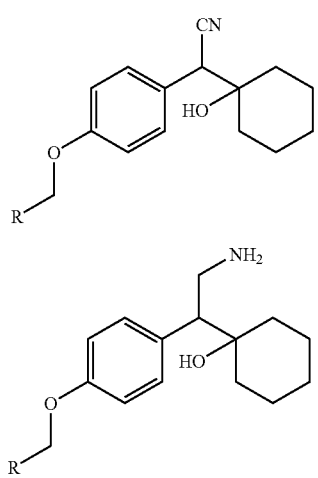

wherein the R is preferably selected from phenyl, nitrophenyl, hydroxyphenyl or halophenyl;
b) alkylating the 1-[2-amino-1-(substituted benzyloxyphenyl)ethyl]cyclohexanol of formula (III) to obtain compound of formula (IV); and

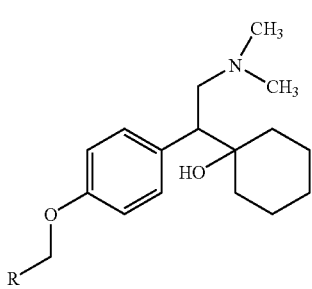

c) deprotecting the compound of formula (IV) to obtain O-desmethylvenlafaxine.

According to the process of the present invention, the reducing agent is selected from a mixture of sodiumborohydride-trifluoroacetic acid, sodiumborohydride-iodine, sodiumborohydride-cobalt chloride, sodiumborohydride-nickel chloride, sodiumborohydride-aluminum chloride or Raney nickel. Preferably the reducing agent used herein is sodiumborohydride-iodine. The alkylation is performed using the alkylating agent selected from formaldehyde and formic acid, methyl iodide or dimethyl sulphate to give formula (IV).

The solvent used herein in the reduction reaction is selected from the group comprising ether, alcohol, aliphatic hydrocarbon, aromatic hydrocarbon and halogenated hydrocarbon. The ether solvent is selected from tetrahydrofuran, 1,4-dioxane, diethyl ether, diisopropyl ether or isopropyl ether, the aliphatic hydrocarbon is selected from hexane, cyclohexane, heptane, pentane or mixtures thereof.

According to one embodiment of the present invention the reduction process is carried out employing Raney Nickel in presence of solvent selected from the alcohol such as methanol, ethanol, isopropyl alcohol or mixtures thereof.

According to a process of the present invention, wherein deprotection of 1-[2-(dimethylamino)-1-(substituted benzyloxyphenyl)ethyl]cyclohexanol of formula (IV) is performed in presence of a metal catalyst under hydrogen pressure to obtain O-desmethylvenlafaxine. The metal catalyst used herein is selected from raney nickel, palladium on carbon.

According to our present invention, O-desmethylvenlafaxine is subjected to salt formation employing an acid, preferably succinic acid in presence of a solvent to obtain pharmaceutically acceptable acid addition salt of O-desmethylvenlafaxine. The solvent used herein is selected from methanol, ethanol, n-propanol, isopropanol or mixture thereof.

According to the process for the present invention, wherein the 1-[cyano(substituted benzyloxyphenyl)methyl]cyclohexanol of formula (II) is prepared by reacting substituted benzyloxyphenyl acetonitrile of formula (I),

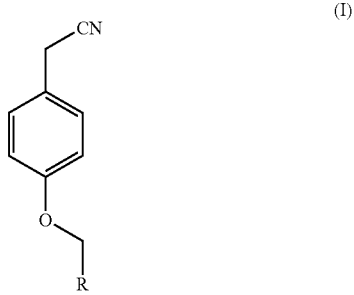

with cyclohexanone in presence of a base and optionally in presence of phase transfer catalyst (PTC) in a solvent, wherein the R is preferably selected from phenyl, nitrophenyl, hydroxyphenyl and halophenyl.

According to the present invention, substituted benzyloxyphenyl acetonitrile of formula (I) is prepared by reacting p-hydroxy phenyl acetonitrile with R—CH2-X to give formula (I), R=phenyl, nitrophenyl, hydroxyphenyl and halophenyl; X=Cl, Br and I.

The substituted benzyloxyphenyl acetonitrile of formula (I) according to the present invention is reacted by way of condensation with cyclohexanone in the presence of base and optionally phase transfer catalyst to give the 1-[cyano(substituted benzyloxyphenyl)methyl]cyclohexanol of formula (II). The base employed herein is selected from the group comprising alkali metal hydroxide, alkali metal alkoxide, alkali earth metal hydroxide, alkali earth metal oxide or lithium hexmethylenedisilane is also used herein during the condensation reaction. Preferably the alkali metal hydroxide is sodium hydroxide, potassium hydroxide, the alkali metal alkoxide is sodium methoxide, sodium tertiarybutoxide, potassium methoxide, potassium tertiarybutoxide. The alkali earth metal hydroxide used herein is magnesium hydroxide or calcium hydroxide and the alkali earth metal oxide used herein is selected from calcium oxide or magnesium oxide.

The condensation reaction is carried out in presence of a solvent selected from alcohol, aliphatic hydrocarbons, aromatic hydrocarbons or ethers. The alcohol employed herein is selected from methanol, ethanol, isopropyl alcohol or mixtures thereof, the aliphatic hydrocarbon is selected from hexane, heptane, and cyclohexane, the aromatic hydrocarbons is selected from toluene, xylene and the ether solvent is selected from tetrahydrofuran, 1,4-dioxane, diethyl ether, diisopropyl ether and isopropyl ether.

The phase transfer catalyst used in the process according to present invention is selected from tetrabutylammonium hydrogensulphate, tetrabutylammonium bromide, tetrabutylammonium chloride, tetrabutyl ammonium iodide, benzyltriethyl ammonium chloride, polyethylene glycol-400 or ALIQUATE 336™ (N-methyl-N,N-dioctyloctan-1-ammonium chloride).

According to one embodiment of the present invention, the 1-[2-amino-1-(substituted benzyloxyphenyl)ethyl]cyclohexanol of formula (III) is optionally treated with acid selected from hydrochloric acid, hydrobromic acid, sulphuric acid, phosphoric acid, methane sulphonic acid, p-toluene sulphonic acid to obtain corresponding acid addition salt of formula (IIIa). Further, the acid addition salt of formula (IIIa) can be optionally subjected to desaltification in presence of aqueous base to obtain a pure compound of Formula (III).

According to the process of the present invention, the reduction reaction being carried out in a mixture of sodium borohydride and iodine results in formation of fewer impurities as compared to prior art process and thereby requires fewer purification steps to obtain the desired quality of the final product. According to the present invention, the reduction reaction is being carried out without employing the high pressure reactors. Further according to the present invention, the conversion of compound of formula (III) to acid addition salt thereby improving the intermediate purity before final conversion to O-desmethylvenlafaxine.

The following detailed reaction mechanism describes an exemplary embodiment of the present invention:

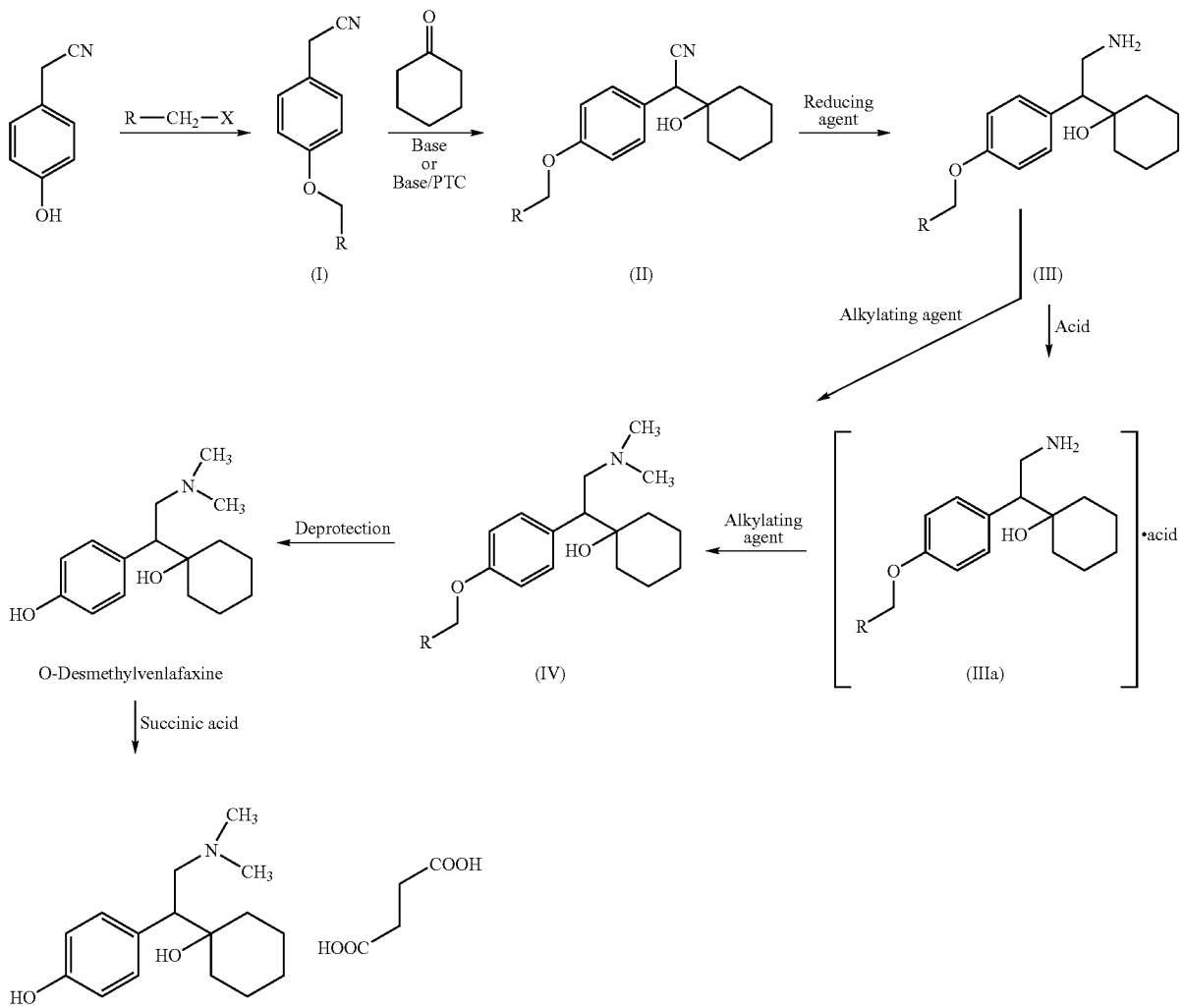

In the foregoing section embodiment are described by way of examples to illustrate the process of invention. However, these are not intended in any way to limit the scope of the present invention and several variants of these examples would be evident to person ordinary skilled in the art.

EXAMPLE-1

Preparation of p-benzyloxyphenyl acetonitrile

Acetone (500 ml) and potassium carbonate (154 g) were charged into RB flask followed by addition of p-hydroxy phenyl acetonitrile (100 g) under stirring. Benzyl bromide (154 g) was then added at ambient temperature, subsequently heating the reaction mass to 55-58° C. and maintaining for 2 hours. The reaction mass was then cooled to 25° C., filtered and washed with acetone (100 ml) to give 130 g (77.8%) of the p-benzyloxyphenyl acetonitrile.

EXAMPLE-2

Preparation of 1-[cyano(p-benzyloxyphenyl)methyl]cyclohexanol (Method-1)

p-Benzyloxyphenyl acetonitrile (100 g) and methanol (300 ml) was charged into flask Subsequently the reaction mixture was cooled to 0-5° C. and 10% aqueous solution of sodium hydroxide (180 g) and PEG-400 (10 ml) were added. The reaction mixture was then stirred for 30 min. and cyclohexanone (64 g) was added dropwise at 0-5° C. Subsequently, the reaction mass temperature was raised to 25-27° C. and stirred for 15 hours. After completion of the reaction hexane (600 ml) was added, the reaction mixture filtered, washed with hexane (100 ml) followed by DM water to obtain 120 g (83.9%) of the 1-[cyano(p-benzyloxyphenyl)methyl]cyclohexanol.

EXAMPLE-3

Preparation of 1-[cyano(p-benzyloxyphenyl)methyl]cyclohexanol (Method-2)

p-Benzyloxyphenyl acetonitrile (50 g) was added to dry tetrahydrofuran (250 ml) and cooled to −78° C. Lithium HMDS (20.8 g) in tetrahydrofuran (60 ml) was added slowly to the reaction mixture at −70° C. followed by dropwise addition of cyclohexanone (26.6 g. 0.27 mol) and maintaining the temperature at −60° C. for 2 h. The reaction temperature was allowed to rise to 0° C., charged with water (300 ml) and the organic layer was separated. The aqueous layer was then extracted with ethylacetate. The two organic layers were combined, washed with DM water and dried using $Na_2SO_4$. The solvent was evaporated under reduced pressure to give 50 g (70.0%) of 1-[cyano(p-benzyloxyphenyl)methyl]-cyclohexanol.

EXAMPLE-4

Preparation of 1-[2-amino-1-(4-benzyloxyphenyl)ethyl]cyclohexanol

1-[Cyano(p-benzyloxyphenyl)methyl]cyclohexanol (50 g) was dissolved in tetrahydrofuran (300 ml) and sodium borohydride (30 g) was added at room temperature. Reaction mixture was cooled to 0-5° C. and charged with iodine solution drop wise (60 g) in 2.5 h. The reaction mass was stirred for 16 h at 25-30° C., filtered and washed with tetrahydrofuran (50 ml). The filtrate was cooled, DM water (500 ml) was added drop wise at 0-5° C. and tetrahydrofuran was distilled under reduced pressure at 40-45° C. to give residue. The residue was extracted with ethylacetate (250 ml×3), dried, concentrated, cooled and filtered to give 40 g (79.2%) of the 1-[2-amino-1-(4-benzyloxyphenyl)ethyl]-cyclohexanol.

EXAMPLE-5

Preparation of p-toluene sulphonic acid addition salt of 1-[2-amino-1-(4-benzyloxy phenyl)ethyl]cyclohexanol 1-[2-amino-1-(4-benzyloxyphenyl)ethyl]-cyclohexanol (50 g) in ethylacetate (500 ml) is subjected to salt formation by addition of p-toluene sulphonic acid (33 gms) at 25-30° C. The reaction mass was cooled to 0-5° C. and stirred for 1 hour. The precipitated solid was filtered, washed with ethyl acetate and dried under vacuum for 30 minutes to give 53 g of p-toluene sulphonic acid salt of 1-[2-amino-1-(4-benzyloxy phenyl)ethyl]cyclohexanol.

EXAMPLE-6

Preparation of pure 1-[2-amino-1-(4-benzyloxyphenyl)ethyl]cyclohexanol from p-toluene sulphonic acid addition salt of 1-[2-amino-1-(4-benzyloxy phenyl)ethyl]cyclohexanol p-Toluene sulphonic acid salt of 1-[2-amino-1-(4-benzyloxy phenyl)ethyl]cyclohexanol was dissolved in water (500 ml) followed by addition of ethyl acetate (1000 ml) to the reaction mass. The pH of the reaction mass was adjusted to 9.5-10 with aqueous sodium hydroxide solution (50%), which was further extracted with ethyl acetate (2×250 ml), concentrating the ethyl acetate layer and isolating the material in n-hexane (200 ml) to give 40 g (79.2%) of the pure 1-[2-amino-1-(4-benzyloxy phenyl)ethyl]cyclohexanol.

EXAMPLE-7

Preparation of 1-[2-(dimethylamino)-1-(4-benzyloxyphenyl)ethyl]cyclohexanol

1-[2-Amino-1-(4-benzyloxyphenyl)ethyl]cyclohexanol (15 g) was dissolved in 97% formic acid (20.4 g) and water (90 ml). 40% aq. formaldehyde (15 g) was added to the reaction mass. The solution was heated to 95-100° C., maintained for 15-20 hr. The aqueous layer was cooled to 10° C. and the pH made alkaline with 50% sodium hydroxide solution to 9.5-10.0. The resultant mass then extracted with ethylacetate (100 ml×3) and combined ethyl acetate layer was washed with water, brine and dried on $Na_2SO_4$. The ethyl acetate was evaporated to give 13.5 g (83.3%) of the 1-[2-(dimethylamino)-1-(4-benzyloxyphenyl)ethyl]cyclohexanol.

EXAMPLE-8

Preparation of 1-[2-(dimethylamino)-1-(4-hydroxyphenyl)ethyl]cyclohexanol (O-desmethylvenlafaxine)

1-[2-(Dimethylamino)-1-(4-benzyloxyphenyl)ethyl]cyclohexanol (30 g) was dissolved in methanol (600 ml), charged with 10% palladium on carbon (3 g) and hydrogenated pressure for 6 h at room temperature. The catalyst was filtered, washed with methanol, and combined filtrate evaporated under reduced pressure to give 18 g (81.08%) of the 1-[2-(dimethylamino)-1-(4-hydroxyphenyl)ethyl]cyclohexanol.

EXAMPLE-9

Preparation of O-Desmethylvenlafaxine succinate

1-[2-(dimethylamino)-1-(4-hydroxyphenyl)ethyl]cyclohexanol (100 gms) was dissolved in isopropyl alcohol (1.62 lts) and succinic acid (45 gms) was added at room temperature. The reaction mass was heated to reflux and maintained for 30 minutes. The above reaction mass was charged with carbon (5 gms) and maintained for 15 minutes. The reaction mass was then filtered and the filtrate cooled to 0-5° C. under stirring and maintained under stirring for 3-4 hours. The obtained precipitate was filtered, washed with chilled IPA to give 120 g (83.33%) of the O-Desmethylvenlafaxine succinate.

While this invention has been described in detail with reference to certain preferred embodiments, it should be appreciated that the present invention is not limited to those precise embodiments rather, in view of the present disclosure, which describes the current best mode for practicing the invention, many modifications and variations, would present themselves to those skilled in the art without departing from the scope and spirit of this invention. This invention is susceptible to considerable variation in its practice within the spirit and scope of the appended claims.

We claim:

1. A process for preparing 1-[2-(dimethylamino)-1-(4-phenol)ethyl]cyclohexanol (O-desmethylvenlafaxine) or its pharmaceutically acceptable salt thereof,

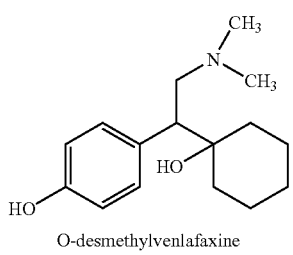

O-desmethylvenlafaxine wherein the process comprises:
(a) reducing 1-[cyano(substituted benzyloxyphenyl) methyl] cyclohexanol of formula (II) with reducing agent sodiumborohydride-iodine or sodiumborohydride-trifluoroacetic acid in presence of a solvent to obtain 1-[2-amino-1-(substituted benzyloxyphenyl) ethyl]cyclohexanol of formula (III);

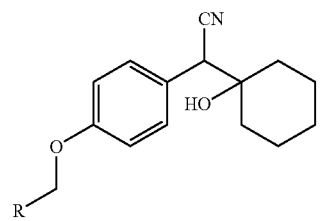

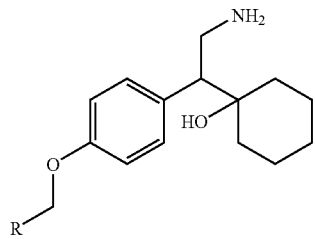

wherein R is selected from phenyl, nitrophenyl, hydroxyphenyl or halophenyl;
(b) alkylating the 1-[2-amino-1-(substituted benzyloxyphenyl)ethyl]cyclohexanol of formula (III) to obtain compound of formula IV; and

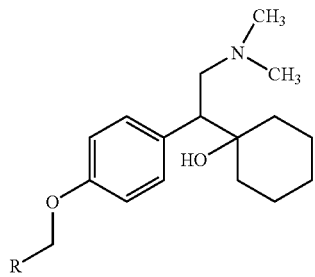

(c) deprotecting the compound of formula (IV) to obtain O-desmethylvenlafaxine.

2. The process according to claim 1, wherein the reducing agent comprises sodium borohydride-iodine.

3. The process according to claim 1, wherein the solvent is selected from ether, aliphatic hydrocarbon or alcohol or mixture thereof.

4. The process according to claim 2, wherein the solvent is selected from tetrahydrofuran, hexane, cyclohexane, heptane, pentane, methanol, ethanol or isopropyl alcohol.

5. The process according to claim 1, wherein the alkylation is performed employing an alkylating agent selected from formaldehyde and formic acid, methyl iodide or dimethyl sulphate.

6. The process according to claim 1, wherein the deprotection is carried out in presence of metal catalyst under hydrogen pressure.

7. The process according to claim 6, wherein the metal catalyst is selected from Raney nickel or palladium on carbon.

8. The process for preparing O-desmethylvenlafaxine according to claim 1, wherein the 1-[cyano(substituted benzyloxyphenyl) methyl) cyclohexanol of formula (II) is prepared by reacting substituted benzyloxyphenyl acetonitrile of formula (I),

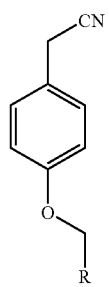

(I)

wherein R is selected from phenyl, nitrophenyl, hydroxyphenyl, or halophenyl, with cyclohexanone in presence of a base and a phase transfer catalyst (PTC) in a solvent.

9. The process according to claim 8, wherein the base is selected from alkali metal hydroxide, alkali metal alkoxide, alkali earth metal hydroxide, alkali earth metal oxide, lithium hexmethylenedisilane or mixture thereof.

10. The process according to claim 9, wherein the alkali metal hydroxide is selected from sodium hydroxide and potassium hydroxide or mixture thereof.

11. The process according to claim 9, wherein the alkali metal alkoxide is selected from sodium methoxide, sodium tertiarybutoxide, potassium methoxide, and potassium tertiarybutoxide or mixture thereof.

12. The process according to claim 9, wherein the alkali earth metal hydroxide is selected from magnesium hydroxide and calcium hydroxide or mixture thereof.

13. The process according to claim 9, wherein the alkali earth metal oxide is selected from calcium oxide, magnesium oxide or mixture thereof.

14. The process according to claim 8, wherein the phase transfer catalyst is selected from tetrabutylammonium hydrogensulphate, tetrabutylammonium bromide, tetrabutylammonium chloride, tetrabutyl ammonium iodide, benzyltriethyl ammonium chloride, polyethylene glycol-400, or N-methyl-N,N-dioctyloctan-1-ammonium chloride.

15. The process according to claim 8, wherein the solvent used is selected from alcohol, aliphatic hydrocarbons, aromatic hydrocarbons or ethers.

16. The process according to claim 15, wherein the solvent is selected from methanol, ethanol, isopropyl alcohol, hexane, heptane, cyclohexane, toluene, xylene tetrahydrofuran, 1,4-dioxane, diethyl ether, diisopropyl ether or isopropyl ether.

17. The process according to claim 1, wherein the process comprises optionally treating the 1-[2-amino-1-(substituted benzyloxyphenyl)ethyl] of formula (III) with an acid to obtain an acid addition salt having formula (IIIa),

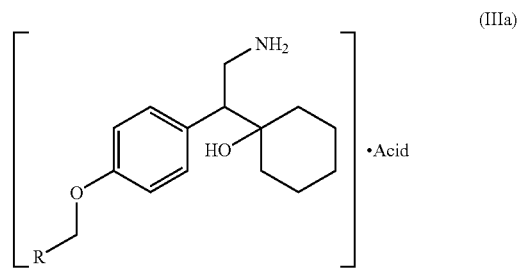

(IIIa)

wherein R is selected from phenyl, nitrophenyl, hydroxyphenyl or halophenyl.

18. The process according to claim 17, wherein the acid used is selected from hydrochloric acid, hydrobromic acid, sulphuric acid, phosphoric acid, methane sulphonic acid or p-toluene sulphonic acid.

19. The process according to claim 1, wherein the process further comprises treating the O-desmethylvenlafaxine with an acid in a solvent to give pharmaceutically acceptable acid addition salt of O-desmethylvenlafaxine.

20. The process according to claim 19, wherein the acid comprises succinic acid.

21. The process according to claim 19, wherein the solvent is selected from methanol, ethanol, n-propanol, isopropanol or mixture thereof.

* * * * *